| United States Patent [19] | [11] | 4,312,949 |
|---|---|---|
| Ahrens | [45] | Jan. 26, 1982 |

[54] METHOD FOR THE PREPARATION OF A GAMMA GLOBULIN SOLUTION SUITABLE FOR INTRAVENOUS USE

[75] Inventor: Ulrich E. Ahrens, Springe, Fed. Rep. of Germany

[73] Assignee: Blutspendedienst det Landesverbande des Deutschen Roten Kreuzes Niedersachsen, Oldenburg und Bremen GmbH, Fed. Rep. of Germany

[21] Appl. No.: 230,687

[22] Filed: Feb. 2, 1981

Related U.S. Application Data

[63] Continuation of Ser. No. 65,975, Aug. 13, 1979, abandoned.

[30] Foreign Application Priority Data

Aug. 16, 1978 [DE] Fed. Rep. of Germany ....... 2835843

[51] Int. Cl.$^3$ .............................................. C07G 7/00
[52] U.S. Cl. ..................................... 435/272; 424/85; 435/269
[58] Field of Search .................. 435/269, 272; 424/85; 260/112 R

[56] References Cited

U.S. PATENT DOCUMENTS 3,903,262  9/1975  Pappenhagen et al. .............. 424/85
3,966,906  6/1976  Schultze et al. ...................... 424/85

Primary Examiner—Robert J. Warden
Attorney, Agent, or Firm—Allegretti, Newitt, Witcoff & McAndrews, Ltd.

[57] ABSTRACT

A gamma globulin solution suitable for intravenous use is prepared by treating the gamma globulin fraction of plasma or serum obtained in known manner with a peptic enzyme at a pH value of about 4. The treatment is carried out with at most 20,000 A.E./100 g. protein at a temperature of about from 37°–40° C.

7 Claims, 1 Drawing Figure

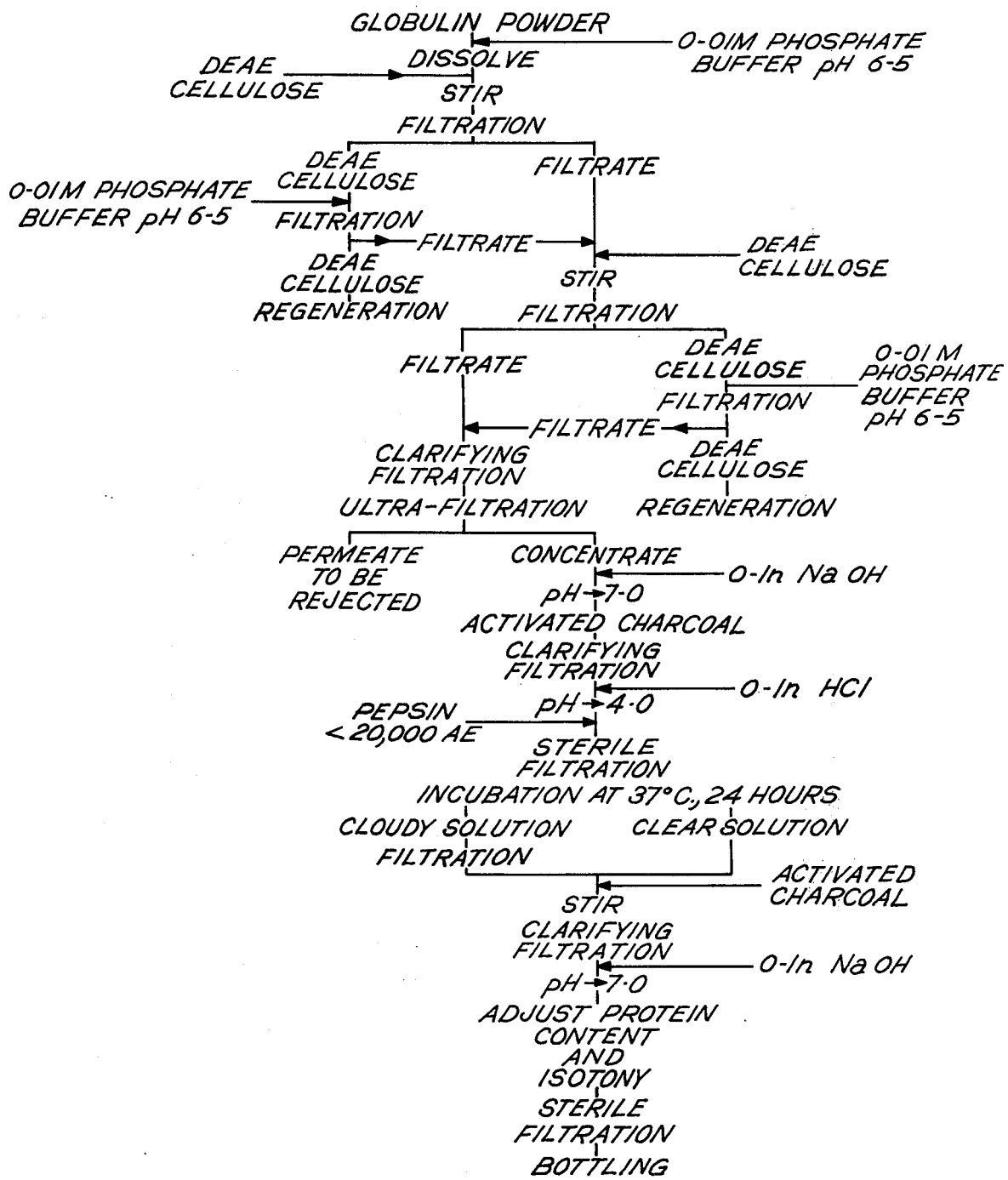

METHOD FOR THE PREPARATION OF A GAMMA GLOBULIN SOLUTION SUITABLE FOR INTRAVENOUS USE

This is a continuation of application Ser. No. 65,975 filed Aug. 13, 1979 now abandoned.

BACKGROUND OF THE INVENTION

1. Field of the Invention

This invention relates to a method for the preparation of a gamma globulin solution suitable for intravenous use, by treating with a peptic enzyme the gamma globulin fraction of a serum obtained in known manner.

2. Description of the Prior Art

Antibody-containing gamma globulin preparations from human plasma are used for intramuscular injections in various pathological conditions. The known preparations, however, have the disadvantage that a sufficient dose for treatment by the intramuscular route leads to considerable pain and about one-third of the administered gamma globulin is broken down before resorption and the greater part is resorbed only slowly.

The discomfort arises not only from the volume of the injection required but also from incompatability reactions.

With intravenous administration of such preparations, very serious secondary reactions are observed in the patient, for example, shivering, rise of temperature, asthma, loss of blood pressure and circulatory disturbances which can indeed even lead to circulatory collapse.

On the other hand, however, the intravenous use of gamma globulin is to be desired, as it presents the only possible alternative in the case of acute illness (such as sepsis) because it is only by this route that the antibodies contained in the gamma globulin can be rapidly and fully effective. It is desirable, however, that the intravenously administered gamma globulin should have a long dwell time in the organism, should not be chemically modified and should be capable of being broken down in the normal way. In addition, the antibacterial, antiviral and antitoxic effect of the gamma globulin should be largely retained. In this way a better utilization of the administered gamma globulin and also a purposeful dosing of the preparation could be achieved.

It is known, in order to prepare a disintegrated gamma globulin which does not influence the complement system, to treat the gamma globulin fraction of the serum which is obtained in known manner, for instance by ammonium sulphate precipitation or alcohol precipitation, at a pH value between 1.5 and 5.5 and a temperature between 0° and 50° C. for two hours to two days with pepsin, for instance with 25,000 to 200,000 E Pepsin per 100 g of protein to be broken down, with continual monitoring of the anti-complementary effect and until the complement-inactivating effect is eliminated, to separate the obtained disintegrated gamma globulin in known manner, for instance by fractionated precipitation with neutral salts or organic solvents or by ultrafiltration of low-molecular separation products, to carry out sterile filtration and, if necessary, to freeze dry.

Other enzymatic processes for the production of a gamma globulin, as described above, are also known, for example by using plasmin.

It is also known that gamma globulins of various origins bind up complement in an uncontrolled and unspecific manner, especially the complement factor C'1 of human and guinea-pig serum. This property is also possessed by the principal fraction of the gamma globulin which is obtained by careful treatment, for example, by preparative electrophoresis or ultracentrifuging or by diethylaminoethyl (DEAE) cellulose filtration or gelfiltration with or without ion exchanger properties.

To summarize it can be established that there are no methods which comply with the initially mentioned requirements of an intravenously applicable gamma globulin.

It is an object of the present invention to produce a gamma globulin suitable for intravenous use, which shall possess all the required, previously mentioned characteristics.

BRIEF SUMMARY OF INVENTION

According to the present invention there is provided a method of producing a gamma globulin solution suitable for intravenous use, which comprises treating a solution of the gamma globulin fraction of plasma or serum with an ion-exchange substance, subjecting the solution to ultrafiltration to yield a concentrate, treating the concentrate with an absorbing substance and separating purified concentrate from the absorbing substance, treating the purified concentrate with a peptic enzyme at a pH value of about 4, treating the solution thus obtained with an absorbing substance and separating the absorbing substance from the solution.

It is preferred to use pepsin as the peptic enzyme and the peptic enzymatic treatment is carried out at a pH value of about 4 and a temperature of from about 37° to 40° C.

Preferably, the gamma globulin solution is adjusted to a pH value of about 6.5 by a phosphate buffer and is initially treated with diethylaminoethyl (DEAE) cellulose. The suspension is filtered and the DEAE cellulose is washed with a phosphate buffer having a pH value of 6.5 and the combined filtrates are subjected once again to a DEAE cellulose treatment and as before are filtered and washed.

The two filtrates are combined and subsequently clarified by filtration which is followed by ultrafiltration. The permeate thus produced is rejected, the concentrate is adjusted to the pH value 7.0 and the solution is treated with an absorbing substance such as activated charcoal. After the filtration and adjusting of the solution of the gamma globulin using 0.1 n HCL to a pH value of 4.0, pepsin is added at a rate of at most 20,000 A.E/100 g protein. The quantity of pepsin required per 100 g protein depends upon the quality of the gamma globulin used. The more careful the production of the gamma globulin to be used, the less will be the required quantity of pepsin per 100 g of protein.

This pepsin treatment lasts preferably for a period of from 4 to 24 hours, preferably 12 to 24 hours. The solution is then subjected to a renewed treatment with activated charcoal, whereupon the filtrate is clarified by filtration and the adjusting of protein content and isotony, sterile filtration and bottling are carried out in known manner.

The method of producing a gamma globulin solution suitable for intravenous use according to the present invention requires numerous stages, but results quite unexpectedly in a decidedly improved gamma globulin preparation. It has been found that the difference in action between known preparations and the gamma globulin prepared according to this invention, especially in respect of non-specific complement binding, is considerable. This is based upon the fact that a portion of the immune globulin is contained in the preparation in native form as IgG and another portion as fragment F (a,b)$_2$, resulting on the one hand in antibacterial and on the other hand in particularly rapid antiviral effectiveness. Nevertheless, the non-specific complement forming (C'1), even of the undiluted solution of the intravenous preparation, is very small.

Retarding of haemolysis, determined in the usual manner (2 CH 50) for the undiluted solution is less than 50%, preferably less than 30%.

The clear superiority of the gamma globulin preparation produced according to the invention is attributable certainly to the multi-stage, careful and relatively weak enzymatic treatment.

This result was especially surprising because both the non-specific complement forming (C'1) of a gamma globulin purified by DEAE cellulose absorption and also the non-specific complement forming of a weakly enzymatically treated gamma globulin or a gamma globulin treated only at a pH value of 4, are considerably greater than that of the preparation of this invention.

BRIEF DESCRIPTION OF DRAWING

The accompanying drawing is a flow diagram illustrative of an embodiment of the present invention.

DETAILED DESCRIPTION OF THE INVENTION

One embodiment of the invention will now be described by way of example and reference may be had to the accompanying flow sheet which is illustrative of a process according to the invention.

200 g of gamma globulin powder are dissolved in 20 liters of 0.01 m phosphate buffer solution at a pH value of 6.5 at 4° C. and filtered. There is then added to the filtrate 0.09 times by weight the quantity of equilibriated DEAE cellulose and this suspension is stirred for 3 hours at 4° C. The cellulose is DEAE cellulose by the firm Whatman, DE 52. After 3 hours stirring the suspension is filtered off through a Büchner funnel and is washed with suction with 1 liter of 0.01 m buffer solution having a pH value 6.5.

Into the gamma globulin solution combined with the wash water, a proportion of 0.023 by weight of equilibriated DEAE cellulose is then introduced and, after an absorption time of 3 hours, is filtered off through a Büchner funnel. The ion exchange substance is washed with 0.5 liters of 0.01 m phosphate buffer solution having a pH value of 6.5, the washing solution and the filtrate are combined and the combined solutions are filtered. The solution is then ultrafiltered through a hollow fibre cartridge produced by the firm Amicon, of type H 10 p 100 for about 7.5 hours and reduced to about 1.3 liters total volume. The cartridge is then washed out with about 300 ml of Permeate. The concentrate is adjusted to a pH value of 7.0 initially by adding 1 n of NaOH and then more precisely by adding 0.1 n of NaOH.

An addition of 0.5 g/dl of activated charcoal is now carried out. 8.0 g of activated charcoal are suspended in 100 ml of buffer solution with a pH value 7.0 and added to the protein solution. Stirring is carried out for 30 minutes. This is followed by filtration in which the activated charcoal is separated. The filtrate is adjusted to a pH of 4.0 by initially adding 1 n of NaOH and then more precisely 0.1 n of NaOH and there is added to it 484 mg of three times crystallized pepsin, that is 17,000 anson units.

The solution is sterilely filtered in sterile 1 liter glass bottles. This is followed by incubation of the clear, slightly yellowish solution at a temperature of 37° C. 24 hours after the start of incubation the milky white solution is cooled to 20° C. and is clarifyingly filtered through a filter layer produced by the firm Seitz, K 10.

2.0 g/dl of activated charcoal, which has previously been suspended in 0.01 m phosphate buffer solution, is now again added to the filtrate. After a stirring time of 30 minutes filtration is carried out, in which the activated charcoal is separated. The filtrate is then adjusted to a pH value of 7.0 initially and rapidly with 1 n of NaOH and then more accurately with 0.1 n of NaOh. The total volume is about 1.4 liter. For adjusting the protein content of 5 g/dl a specimen is removed for protein determination. The adjusting of the protein content to 0.01 m of phosphate buffer of ph 7.0 and of the isotony are then carried out.

The process sequence is illustrated in the attached flow diagram.

What is claimed is:

1. A method of producing a gamma globulin solution suitable for intravenous use, comprising the following steps in the following sequence: treating a solution of gamma globulin fraction of plasma or serus with a DEAE cellulose-type ion-exchange substance, subjecting the solution to ultrafiltration to yield a concentrate, treating the concentrate with an activated charcoal-type absorbing substance and separating purified concentrate from the absorbing substance, treating the purified concentrate with a peptic enzyme at a pH value of about 4, treating the solution thus obtained with an activated charcoal-type absorbing substance and separating the absorbing substance from the solution.

2. A method according to claim 1 in which said peptic enzyme is pepsin and the purified concentrate is treated with not more than 20,000 Anson units per 100 g protein at a temperature of from 37° to 40° C.

3. A method according to claim 1 in which the purified concentrate is treated with peptic enzyme for from 12 to 24 hours.

4. A method according to claim 1 in which the treatment of the solution of the gamma globulin fraction with an ion exchange substance is carried out using diethylaminoethyl cellulose as the ion exchange substance by phosphate buffering the solution at a pH of about 6.5 and treating the phosphate buffered solution with a first portion of diethylaminoethyl cellulose and filtering to produce a first filtrate, washing the diethylaminoethyl cellulose residue with a phosphate buffer solution at a pH of about 6.5 and filtering to produce a second filtrate, combining said first and second filtrates and treating the combined filtrates with a further portion of diethylamineothyl cellulose and filtering to produce a third filtrate, washing the residue of the further portion of diethylaminoethyl cellulose with a phosphate buffer solution at a pH of about 6.5 and filtering to produce a fourth filtrate, combining said third and fourth filtrates and subjecting said combined third and fourth filtrates to ultrafiltration to yield said concentrate.

5. A method according to claim 1 in which the absorbing substance used to treat said concentrate is activated charcoal and the pH value of the concentrate is adjusted to about 7 before treatment with said activated charcoal.

6. A method according to claim 1 in which the protein content and isotonicity of the solution obtained after separation of the absorbing substance is adjusted to a protein content of about 5 g/dl and a pH of about 7.0 and the solution is then filtered and put in containers for storage.

7. A method according to claim 6 in which the pH value of the solution is adjusted to about 7 before the protein content and isotonicity therefore is adjusted.

* * * * *